United States Patent
Allard et al.

(10) Patent No.: US 7,853,446 B2
(45) Date of Patent: Dec. 14, 2010

(54) GENERATION OF CODIFIED ELECTRONIC MEDICAL RECORDS BY PROCESSING CLINICIAN COMMENTARY

(75) Inventors: David J. Allard, Boynton Beach, FL (US); Robert M. Szabo, Boca Raton, FL (US); James J. Toohey, Boca Raton, FL (US)

(73) Assignee: International Business Machines Corporation, Armonk, NY (US)

( * ) Notice: Subject to any disclaimer, the term of this patent is extended or adjusted under 35 U.S.C. 154(b) by 1055 days.

(21) Appl. No.: 11/381,141

(22) Filed: May 2, 2006

(65) Prior Publication Data

US 2007/0260977 A1 Nov. 8, 2007

(51) Int. Cl.
*G06F 17/27* (2006.01)
(52) U.S. Cl. .............................. 704/9; 705/2; 715/230; 715/231; 715/268
(58) Field of Classification Search .................. 715/230, 715/231; 705/2; 704/9
See application file for complete search history.

(56) References Cited

U.S. PATENT DOCUMENTS

| | | | | |
|---|---|---|---|---|
| 5,325,293 A * | 6/1994 | Dorne | ............................ | 705/2 |
| 5,483,443 A * | 1/1996 | Milstein et al. | ................. | 705/3 |
| 5,809,476 A * | 9/1998 | Ryan | ............................. | 705/2 |
| 6,178,416 B1 * | 1/2001 | Thompson et al. | .................. | 1/1 |
| 6,615,178 B1 * | 9/2003 | Tajima | ........................ | 704/277 |
| 6,889,190 B2 | 5/2005 | Hegarty | | |
| 6,915,254 B1 * | 7/2005 | Heinze et al. | .................... | 704/9 |
| 7,409,354 B2 * | 8/2008 | Putnam et al. | .................. | 705/2 |
| 7,555,425 B2 * | 6/2009 | Oon | ............................... | 704/9 |
| 2002/0007285 A1 * | 1/2002 | Rappaport | ....................... | 705/2 |
| 2002/0019749 A1 * | 2/2002 | Becker et al. | .................. | 705/2 |
| 2002/0091549 A1 | 7/2002 | Provost | | |
| 2002/0138303 A1 | 9/2002 | Enos et al. | | |
| 2002/0169638 A1 | 11/2002 | Rodriguez-Cue | | |
| 2003/0020704 A1 * | 1/2003 | Maercovich et al. | ........ | 345/211 |
| 2003/0034877 A1 * | 2/2003 | Miller et al. | ................ | 340/5.61 |
| 2003/0101047 A1 * | 5/2003 | Panttaja | ......................... | 704/9 |
| 2003/0105638 A1 | 6/2003 | Taira | | |
| 2003/0125017 A1 | 7/2003 | Greene | | |
| 2003/0187688 A1 | 10/2003 | Fey et al. | | |
| 2003/0189484 A1 * | 10/2003 | Rust et al. | ............... | 340/323 R |
| 2003/0191669 A1 | 10/2003 | Fitzgerald et al. | | |
| 2004/0117206 A1 * | 6/2004 | Steinberger et al. | ............ | 705/2 |
| 2004/0128165 A1 | 7/2004 | Block et al. | | |
| 2004/0133418 A1 * | 7/2004 | Turcato et al. | .................. | 704/9 |

(Continued)

OTHER PUBLICATIONS

Dickerson et al., "Hospital Communications System", IBM TDB 11-75, pp. 1967-1972 (Nov. 1975).

*Primary Examiner*—Stephen S Hong
*Assistant Examiner*—I-Chan Yang
(74) *Attorney, Agent, or Firm*—Cuenot, Forsythe & Kim, LLC

(57) ABSTRACT

A method and system for generating codified electronic records. A textual commentary can be received from a user and, in real time, the textual commentary can be analyzed to identify a plurality of codes that potentially correlate to the textual commentary. The identified codes then can be presented to the user in real time. A first user input can be received to select at least one of the identified codes, and the selected code can be added to an electronic record.

21 Claims, 2 Drawing Sheets

U.S. PATENT DOCUMENTS

| | | |
|---|---|---|
| 2004/0172307 A1 | 9/2004 | Gruber |
| 2004/0204961 A1* | 10/2004 | Rensimer et al. ............... 705/2 |
| 2004/0254816 A1 | 12/2004 | Myers |
| 2005/0137910 A1* | 6/2005 | Rao et al. ..................... 705/3 |
| 2006/0080312 A1 | 4/2006 | Friedlander et al. |
| 2007/0260478 A1 | 11/2007 | Szabo |

* cited by examiner

GENERATION OF CODIFIED ELECTRONIC MEDICAL RECORDS BY PROCESSING CLINICIAN COMMENTARY

BACKGROUND

1. Field of the Invention

The present invention relates to electronic record systems and, more particularly, to devices that generate codified electronic records.

2. Description of the Related Art

The Institute of Medicine has reported that approximately 100,000 deaths occur per year in the United States due to preventable medical errors. This, in part, is the reason for a massive world wide effort to move to electronic health record (EHR) systems. Some EHR systems do exist today; however, such systems are not integrated in a manner that allows efficient sharing of medical records between medical facilities. Further, existing EHR systems do not capture a level of detail required to automatically analyze patient data.

Another obstacle hindering widespread implementation of EHR systems is that such systems do not seamlessly integrate with current medical practices. For instance, clinicians usually are trained to dictate a patient condition into a recorder using a textual commentary that interweaves potential and excluded diagnosis with positive and negative indications in a run-on sentence format. Such sentence structure normally exceeds the trusted ability of standard computerized text analysis tools. Thus, automated analysis of text currently is not a viable option. Instead, a medical transcription service is used to subsequently transcribe the dictation into a text document that can be stored in the clinician's office with other patient records. The transcribed text typically does not contain medical codes that are compliant with EHR systems, however. Moreover, medical transcription is labor intensive, time consuming, and error prone.

It therefore would be beneficial to provide a system for documenting patient information that is both accurate and efficient.

SUMMARY OF THE INVENTION

The present invention provides method(s), system(s), and apparatus relating to generation of codified electronic records. One embodiment of the present invention can include receiving, within a computer, a textual commentary from a user. The user can be a clinician that is the source of the textual commentary. The method can include, responsive to receiving the textual commentary and in real time, analyzing the textual commentary to identify a plurality of codes that potentially correlate to the textual commentary and presenting the identified codes to the user through an output device. A first user input can be received to select at least one of the identified codes presented via the output device responsive to presenting the identified codes, and the selected code can be added to an electronic record responsive to receiving the first user input.

Another embodiment of the present invention can include receiving, within a computer, a textual commentary from a user, wherein the user is a clinician and source of the textual commentary. The method can include, responsive to receiving the textual commentary and in real time, analyzing the textual commentary to identify a first plurality of codes that potentially correlate to the textual commentary and presenting the first plurality of codes to the user through an output device. Responsive to presenting the first plurality of codes, at least a first user input can be received to select at least one code from the first plurality of codes presented on the output device and at least one operation can be initiated on the selected code. A second plurality of codes can be presented to the user reflecting changes caused by the operation on the selected code via the output device responsive to receiving the at least a first user input. The second plurality of codes can be added to the electronic record.

Yet another embodiment of the present invention can include a machine readable storage being programmed to cause a machine to perform the various steps and/or functions described herein.

BRIEF DESCRIPTION OF THE DRAWINGS

There are shown in the drawings, embodiments which are presently preferred, it being understood, however, that the invention is not limited to the precise arrangements and instrumentalities shown.

DETAILED DESCRIPTION OF THE INVENTION

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

The embodiments disclosed herein relate to a method and a system for generating codified electronic records in an intuitive manner that is both accurate and efficient. In particular, the system can receive a textual commentary from a user and, in real time, analyze the commentary and present to the user codes and other data that correlate to information communicated in the commentary. The codes and data can be presented hierarchically via an intuitive interface that allows results to be quickly accepted, changed, refined, negated, or deleted by the user. The system also can allow the user to indicate and/or change priority of the codes and data. Primary and secondary considerations also can be indicated or changed. Accordingly, the present invention can aid clinicians in their generation of electronic health records.

Figure 1:
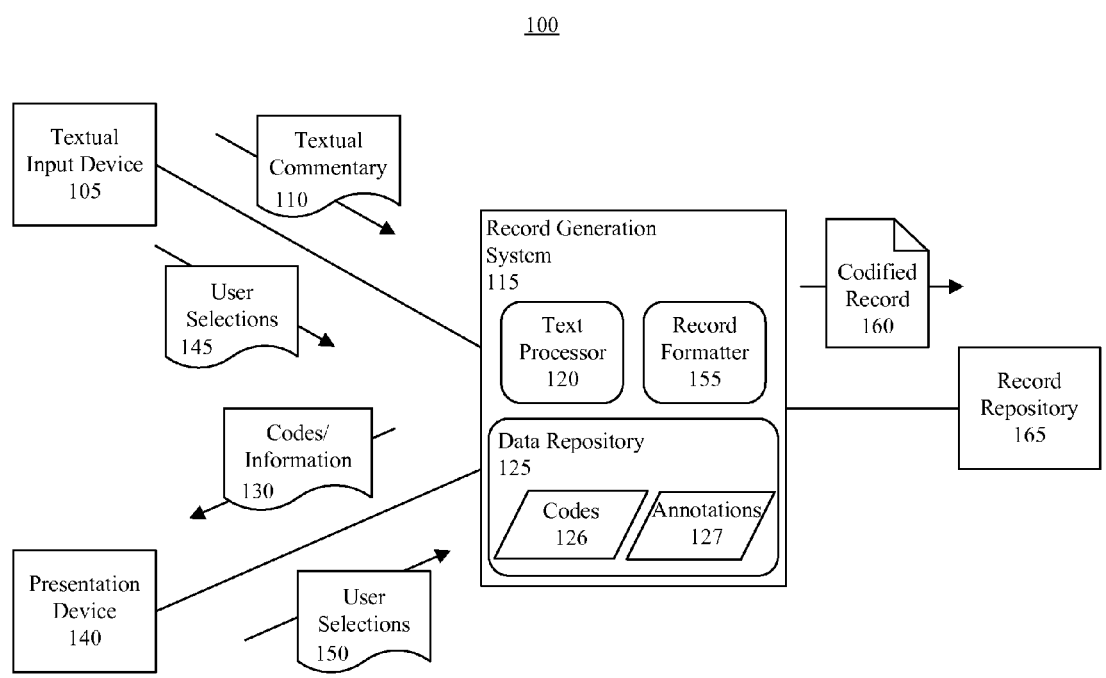
FIG. 1 is a block diagram depicting a system for generating codified electronic records in accordance with an embodiment of the present invention.

FIG. 1 is a block diagram depicting a system 100 for generating codified electronic records in accordance with an embodiment of the present invention. The system 100 can include a textual input device 105 that receives textual commentary 110 from a user and forwards the textual commentary 110 to a record generation system 115. The textual commentary 110 can be entered, for example, as one or more spoken utterances, typed text, hand scribed text, or entered in any other suitable manner. For instance, the textual input device 105 can include an audio transducer (e.g. a microphone), a keyboard, a keypad, an electronic writing tablet, a scanner or any other device which can be used by a user to enter textual commentary 110. The textual commentary 110 can be propagated to the record generation system 115 via a wired or a wireless communication link. In one wireless arrangement, the textual input device can transmit the textual commentary 110 in accordance with the Bluetooth protocol or the IEEE 802.11 protocol. Nonetheless, any suitable wireless and/or wired communication protocol(s) can be used and the invention is not limited in this regard.

In an arrangement in which the textual commentary 110 is entered as spoken utterances, a speech recognition application can be used to convert the spoken utterances to text. The speech recognition application can be instantiated on the textual input device 105, in which case the textual commentary 110 can be transmitted as text to the record generation system 115, or the speech recognition application can be instantiated on the record generation system 115, in which case the textual commentary 110 can be transmitted as audio data.

The record generation system 115 can include a text processor 120 that processes the textual commentary 110 in real time. As used herein, the term "real time" means a level of processing responsiveness that a user senses as sufficiently immediate or that enables the processor to keep up with some external process. The text processor 120 can include text analysis routines that analyze the textual commentary 110 and identify at least one attribute contained therein. The attribute can be, for example, information that is conveyed in the textual commentary 110, such as an observation, complaint, sign, symptom, diagnosis, drug, and/or procedure. To identify the attribute, the text analysis routines can perform a sequence of processing steps. For instance, the routines can perform tokenization (including abbreviations, spelling, acronyms), sentence segmentation, part-of-speech assignment, named-entity identification, phrasal parsing, sentential parsing, semantic interpretation, lexical normalization, discourse interpretation, template filling, merging and/or any other suitable text processing techniques. Such routines can be integrated into a text analysis framework, for example the Unified Information Management Architecture (UIMA) as provided by International Business Machines of Armonk, N.Y., and specifically optimized to recognize medical terminology.

The text processor 120 then can associate the attributes contained in the textual commentary 110 with appropriate codes selected from one or more chosen coding schemes. As used herein, the term "code" means a grouping of one or more characters that has been defined to correlate to one or more attributes. In one embodiment, the coding schemes can be medical coding schemes, for instance current procedural terminology (CPT), diagnostic coding, symptom coding and prescription coding. Still, other coding schemes can be used and the invention is not limited in this regard.

Selection of the codes can be trainable. For example, the record generation system 115 can maintain a history of codes that have been previously accepted for a particular attribute that has been contained in previous textual commentaries. Such history then can be referenced when selecting codes with which to associate that attribute when the attribute is contained in the textual commentary 110. Each code that is selected can be weighted based on the relative frequency that the code has been accepted as indicated in the code history. Such weighting can be indicated when the codes are presented to the user.

In one aspect of the invention, the code selection history can be user specific. For instance, code acceptance records can be maintained for each user. Thus, by way of example, if one user tends to use a particular utterance when referring to a particular diagnosis, the text processor 120 will have a high probability at selecting the appropriate diagnostic codes.

The codes and code acceptance history records can be retrieved from a data repository 125. The data repository 125 can include, for example, one or more data tables 126 that correlate attributes with appropriate codes. Such codes and attributes can be automatically updated to insure that the codes and attributes contained in the data repository 125 are current, accurate and complete. The data tables 126 also can indicate the code acceptance history. In one arrangement, one or more data tables 126 can be provided for each of the coding schemes that may be used.

The data repository 125 also can include one or more data tables 127 that store annotations. The annotations can be used to describe the attributes contained in the textual commentary 110 and/or describe the selected codes. As with the codes, the annotations can be automatically selected by the text processor 120 in real time. In one arrangement, annotators that use the annotations can be trained using suitable training data. Annotators can be a specifically relevant type of code that is selected, for example a code correlating to an observation, complaint, sign, symptom, diagnosis, drug and/or procedure. The annotations also may include dictionaries, specialized vocabularies, terminology, abbreviations and/or ontologies for each of these. Nonetheless, other types of annotations can be used and the invention is not limited in this regard. The annotators can be updated to insure that the annotations contained in the data repository 125 are current, accurate and complete.

The attributes identified in the textual commentary 110, as well as the codes selected by the annotators, and other information, such as primary and/or secondary considerations, can be forwarded to a presentation device 140 for presentation to the user. In one arrangement, the textual input device 105 and the presentation device 140 can be integrated into a single device or system. Alternatively, the textual input device 105 and presentation device 140 can be separate devices or systems. Hereinafter, codes, annotations and other information are collectively referred to as codes/information 130. The codes/information 130 can be propagated from the record generation system 115 to the presentation device 140 via a wired or a wireless communication link. As noted, any suitable communication protocol(s) can be used.

The user can interface with the presentation device 140 to scan, modify and confirm the analysis of the textual commentary 110 represented by the codes/information 130. The presentation device 140 can include, for example, an audio transducer (e.g. a loudspeaker), a display and/or any other device suitable for presenting the codes/information 130 to the user. In one aspect of the invention, the codes/information 130 can be presented to the user in a hierarchical order. Such order can be based, at least in part, on code acceptance history, user preferences, code classifications, or any other suitable parameter.

In an arrangement in which the presentation device 140 comprises an audio transducer, the codes/information 130 can be audibly presented to the user. For instance, the codes/information 130 can be propagated as text to the presentation device 140, in which case a text-to-speech application can be instantiated on the presentation device 140, or the codes/information 130 can be transmitted to the presentation device 140 as audio data, in which case a text-to-speech application can be instantiated on the record generation system 115. The user can be prompted to utter selections 145 into the textual input device 105 to select particular ones of the codes/information 130 and accept, change, refine, negate, or delete such selections. The hierarchical order of the codes/information 130 also can be changed by the user in the same manner. Updated codes/information can be audibly presented to the user reflecting changes to the codes/information 130 originally presented. The process can repeat until the user accepts the codes/information 130 as presented.

The codes/information 130 also can be visually presented to the user via a display. For example, the codes/information 130 can be presented on a handheld portable display. In another arrangement the codes/information 130 can be presented on a wall mounted display or a display attached to a patient bed. For example, the record generation system 115 can be configured to communicate with a plurality of displays, each of which is in a different location, and one or more of such displays can be activated when their use is desired.

In another example, a proximity detector can be implemented to activate a particular display 140 when an authorized user is detected within an area served by the display. For instance, the textual input device 105 can communicate an authorization signal to activate the display 140 when the textual input device 105 is located within an area in which the display 140 can be viewed. Further, the textual input device 105 can communicate an identifier for a particular user session with which the textual input device 105 is associated, and the identifier can be used by the display 140 to become associated with that user session. For instance, the display 140 can send a session request to the record generation system 115. Notwithstanding, display selection can be implemented in any other suitable manner and the invention is not limited in this regard.

The display can include a graphical user interface (GUI) for presenting the codes/information 130 to the user. The GUI can include, for example, a touch screen or cursor to navigate the GUI and to receive user selections 150. The user selections 150 can be processed to select particular ones of the codes/information 130 and accept, change, refine, negate, or delete such selections, or to change the hierarchical order in which the codes/information 130 are presented. User selections 145 generated from spoken utterances also can be received from the textual input device 105. In response to the user selections 145, 150, updated codes/information can be presented to the user on the display reflecting changes to the codes/information 130 originally presented. The process can repeat until the user accepts the codes/information 130 as presented.

Once the user has accepted the codes/information 130, a record formatter 155 can add the codes/information 130 into a codified record 160. The codified record 160 then can be forwarded to a record repository 165. The record repository 165 can be a component of the record generation system 115, or be communicatively linked to the record generation system 115 in a suitable manner. The record repository 165 can provide access to the codified record 160 for purposes of treatment, diagnosis, billing, filling of prescriptions, or any other desired purposes.

Figure 2:
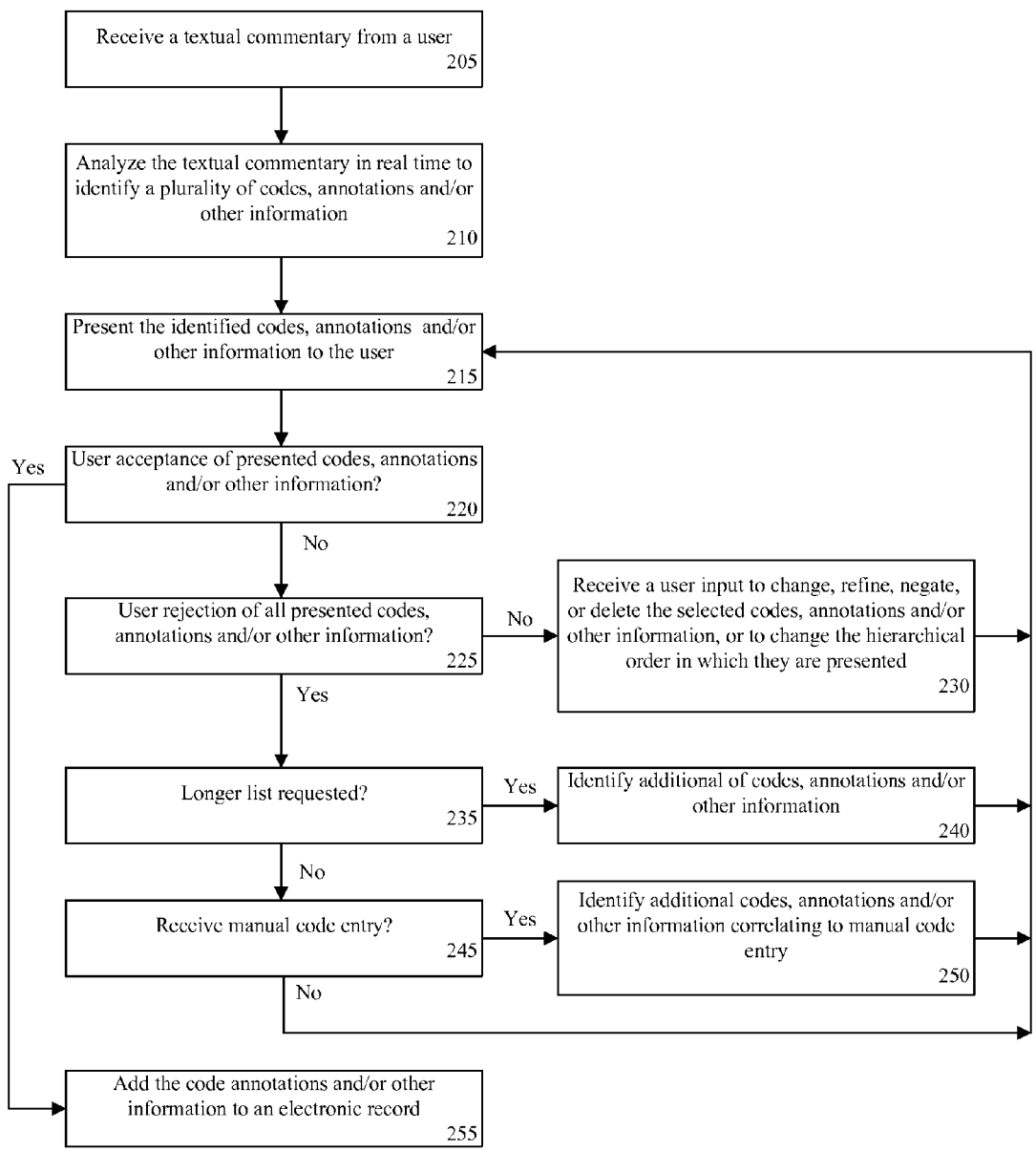
FIG. 2 is a flow chart illustrating a method of generating codified electronic records in accordance with another embodiment of the present invention.

FIG. 2 is a flow chart illustrating a method 200 of generating codified electronic records in accordance with another embodiment of the present invention. In step 205, a textual commentary can be received from a user. In step 210, the textual commentary can be analyzed in real time to identify a plurality of codes, annotations and/or other information (hereinafter codes/information) correlating to attributes contained in the textual commentary. In step 215, the identified codes/information can be presented to the user, also in real time.

Referring to decision box 220, if a user acceptance of the presented codes/information is received, the process can continue to step 255 and the codes/information can be added to an electronic record. If, however, the user does not accept the codes/information, the process can continue to decision box step 225. If the user does not reject all of the presented codes/information, the process can proceed to step 230 and a user input can be received to change, refine, negate, or delete the selected codes/information, or to change the hierarchical order in which they are presented. The process then can proceed to step 215 and the updated codes, annotations and/or other information can be presented to the user. The process can continue until the user accepts the codes, annotations and/or other information as presented.

Referring again to decision box 225, if the user rejects all presented codes/information, the method can proceed to decision box 235. If the user requests a longer list of codes/information, additional codes/information can be identified, as shown in step 240, and presented to the user in step 215. If, however, the user does not request a longer list, the method can continue to decision box 245. If a manual code entry is received from the user, additional codes/information correlating to the manual code entry can be identified in step 250 and presented to the user in step 215. If a manual code entry is not received, the process can proceed to step 215 and the originally identified code/information can again be presented.

The present invention can be realized in hardware, software, or a combination of hardware and software. The present invention can be realized in a centralized fashion in one computer system or in a distributed fashion where different elements are spread across several interconnected computer systems. Any kind of computer system or other apparatus adapted for carrying out the methods described herein is suited. A typical combination of hardware and software can be a general-purpose computer system with a computer program that, when being loaded and executed, controls the computer system such that it carries out the methods described herein. The present invention also can be embedded in a computer program product, which comprises all the features enabling the implementation of the methods described herein, and which when loaded in a computer system is able to carry out these methods.

The terms "computer program", "software", "application", variants and/or combinations thereof, in the present context, mean any expression, in any language, code or notation, of a set of instructions intended to cause a system having an information processing capability to perform a particular function either directly or after either or both of the following: a) conversion to another language, code or notation; b) reproduction in a different material form. For example, a computer program can include, but is not limited to, a subroutine, a function, a procedure, an object method, an object implementation, an executable application, an applet, a servlet, a source code, an object code, a shared library/dynamic load library and/or other sequence of instructions designed for execution on a computer system.

The terms "a" and "an", as used herein, are defined as one or more than one. The term "plurality", as used herein, is defined as two or more than two. The term "another", as used herein, is defined as at least a second or more. The terms "including" and/or "having", as used herein, are defined as comprising, i.e. open language.

This invention can be embodied in other forms without departing from the spirit or essential attributes thereof. Accordingly, reference should be made to the following claims, rather than to the foregoing specification, as indicating the scope of the invention.

What is claimed is:

1. A method for generating a codified electronic record using a computer comprising an output device, the method comprising:
   receiving, within the computer, a textual commentary from a clinician, wherein the clinician is a source of the textual commentary;
   responsive to receiving the textual commentary from the clinician, and in real time, analyzing the textual commentary to identify a plurality of codes that potentially correlate to the textual commentary, wherein analyzing the textual commentary comprises:
      maintaining a code acceptance history of identified codes previously accepted by the clinician on a per clinician basis, wherein within the code acceptance history, each code is correlated with an attribute identified within the textual commentary; and
      selecting the plurality of codes, at least in part, according to the code acceptance history, wherein one or more identified codes previously accepted by the clinician and correlated to a particular textual commentary attribute are selected when the textual commentary corresponding to the particular textual commentary attribute is received and analyzed;
   presenting the identified codes to the clinician through the output device;
   responsive to presenting the identified codes, receiving a first clinician input selecting at least one of the identified codes presented via the output device; and
   adding the selected code to the electronic record responsive to receiving the first clinician input.

2. The method of claim 1, further comprising receiving a second clinician input to initiate at least one operation on the selected code, the operation selected from the group consisting of accepting, changing, refining, negating, and deleting the selected code.

3. The method of claim 1, wherein:
   analyzing the textual commentary further comprises applying at least one text processing technique to identify at least one attribute contained in the textual commentary; and
   identifying the plurality of codes comprises determining codes that correlate to the identified attribute.

4. The method of claim 1, wherein the output device is a display, the method further comprising selectively enabling the display according to proximity of an authorized clinician to the display.

5. The method of claim 1, wherein the plurality of the identified codes are selected from a plurality of coding schemes, and at least one of the plurality of coding schemes is selected from the group consisting of current procedural terminology (CPT) coding, diagnostic coding, symptom coding and prescription coding.

6. The method of claim 1, wherein receiving the textual commentary comprises receiving at least one form of commentary selected from the group consisting of a spoken utterance, typed text and hand scribed text.

7. The method of claim 1, wherein presenting the identified codes comprises presenting the identified codes in a hierarchical order.

8. The method of claim 1, further comprising:
   identifying an annotation that potentially correlates to the textual commentary; and
   presenting the annotation to the clinician.

9. The method of claim 8, further comprising receiving a second user clinician input selecting the annotation and initiating at least one operation on the selected annotation, the operation selected from the group consisting of accepting, changing, refining, negating, and deleting the selected annotation.

10. A method for generating a codified electronic record using a computer comprising an output device, the method comprising:
    receiving, within the computer, a textual commentary from a clinician, wherein the clinician is a source of the textual commentary;
    responsive to receiving the textual commentary and in real time, analyzing the textual commentary to identify a first plurality of codes that potentially correlate to the textual commentary, wherein analyzing the textual commentary comprises:
       maintaining a code acceptance history of identified codes previously accepted by the clinician on a per clinician basis, wherein within the code acceptance history, each code is correlated with an attribute identified within the textual commentary; and
       selecting the plurality of codes, at least in part, according to the code acceptance history, wherein one or more identified codes previously accepted by the clinician and correlated to a particular textual commentary attribute are selected when the textual commentary corresponding to the particular textual commentary attribute is received and analyzed;
    presenting the first plurality of codes to the clinician through the output device;
    responsive to presenting the first plurality of codes, receiving at least a first clinician input to select at least one code from the first plurality of codes presented via the output device and initiating at least one operation on the selected code;
    responsive to receiving the at least a first clinician input, presenting, via the output device, a second plurality of codes to the clinician reflecting changes caused by the operation on the selected code; and
    adding the second plurality of codes to the electronic record.

11. The method of claim 10, wherein the operation is selected from the group consisting of accepting, changing, refining, negating, and deleting the selected code.

12. A machine readable storage, having stored thereon a computer program having a plurality of code sections executable by a machine for causing the machine to perform the steps of:
    receiving a textual commentary from a clinician, wherein the clinician is a source of the textual commentary;
    responsive to receiving the textual commentary and in real time, analyzing the textual commentary to identify a plurality of codes that potentially correlate to the textual commentary, wherein analyzing the textual commentary comprises:
       maintaining a code acceptance history of identified codes previously accepted by the clinician on a per clinician basis, wherein within the code acceptance history, each code is correlated with an attribute identified within the textual commentary; and
       selecting the plurality of codes, at least in part, according to the code acceptance history, wherein one or more identified codes previously accepted by the clinician and correlated to a particular textual commentary attribute are selected when the textual commentary corresponding to the particular textual commentary attribute is received and analyzed;

presenting the identified codes to the clinician;

responsive to presenting the identified codes, receiving a first clinician input selecting at least one of the identified codes; and adding the selected code to an electronic record responsive to the first clinician input.

13. The machine readable storage of claim 12, further causing the machine to perform the step of receiving a second clinician input to initiate at least one operation on the selected code, the operation selected from the group consisting of accepting, changing, refining, negating, and deleting the selected code.

14. The machine readable storage of claim 12, wherein:

analyzing the textual commentary further comprises applying at least one text processing technique to identify at least one attribute contained in the textual commentary; and identifying the plurality of codes comprises determining codes that correlate to the identified attribute.

15. The machine readable storage of claim 12, further comprising selectively enabling a display according to proximity of an authorized clinician to the display.

16. The machine readable storage of claim 12, wherein the plurality of the identified codes are selected from a plurality of coding schemes, and at least one of the plurality of coding schemes is selected from the group consisting of current procedural terminology (CPT) coding, diagnostic coding, symptom coding and prescription coding.

17. The machine readable storage of claim 12 wherein receiving the textual commentary comprises receiving at least one form of commentary selected from the group consisting of a spoken utterance, typed text and hand scribed text.

18. The machine readable storage of claim 12, further causing the machine to perform the steps of:

identifying an annotation that potentially correlates to the textual commentary; and presenting the annotation to the clinician.

19. The method of claim 1, wherein:

the identified codes are presented to the clinician via the output device, and the identified codes are presented in a list from which the clinician selects at least one of the identified codes that is to be added to the electronic record;

receiving the first clinician input selecting at least one of the identified codes comprises selecting at least one of the identified codes that is presented in the list; and the identified codes in the list that were not selected by the clinician are not added to the electronic record.

20. The method of claim 10, wherein:

the identified codes are presented to the clinician via the output device, and the identified codes are presented in a list from which the clinician selects at least one of the identified codes that is to be added to the electronic record;

receiving the first clinician input selecting at least one of the identified codes comprises selecting at least one of the identified codes that is presented in the list; and the identified codes in the list that were not selected by the clinician are not added to the electronic record.

21. The machine readable storage of claim 12, wherein:

the identified codes are presented to the clinician via the output device, and the identified codes are presented in a list from which the clinician selects at least one of the identified codes that is to be added to the electronic record;

receiving the first clinician input selecting at least one of the identified codes comprises selecting at least one of the identified codes that is presented in the list; and the identified codes in the list that were not selected by the clinician are not added to the electronic record.

* * * * *